US008388984B2

(12) United States Patent
Huguet et al.

(10) Patent No.: US 8,388,984 B2
(45) Date of Patent: *Mar. 5, 2013

(54) SITE-SPECIFIC INTESTINAL DELIVERY OF ADSORBENTS, ALONE OR IN COMBINATION WITH DEGRADING MOLECULES

(75) Inventors: Helene-Celine Huguet, Paris (FR);
Antoine Andremont, Malakoff (FR);
Nicolas Tsapis, Paris (FR); Elias Fattal, Paris (FR)

(73) Assignees: Da Volterra, Paris (FR); Centre National de la Recherche Scientifique, Paris cedex (FR); Assistance Publique—Hopitaux de Paris, Paris RP (FR); Universite Paris Diderot—Paris 7, Paris cedex (FR); Universite Paris-SUD 11, Orsay cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/232,976

(22) Filed: Sep. 14, 2011

(65) Prior Publication Data

US 2012/0107367 A1 May 3, 2012

Related U.S. Application Data

(63) Continuation of application No. 11/804,259, filed on May 17, 2007, now Pat. No. 8,048,413.

(60) Provisional application No. 60/801,121, filed on May 17, 2006.

(51) Int. Cl.
*A61K 9/00* (2006.01)

(52) U.S. Cl. ...... 424/400; 424/78.1; 424/94.1; 424/125; 424/463; 424/464; 424/487; 424/488; 424/493; 424/683; 424/684; 424/724

(58) Field of Classification Search .................. None
See application file for complete search history.

(56) References Cited

U.S. PATENT DOCUMENTS

| | | | |
|---|---|---|---|
| 5,364,636 A | 11/1994 | Ochi | |
| 5,484,773 A | 1/1996 | Heerze et al. | |
| 5,597,564 A | 1/1997 | Ying | |
| 5,929,051 A | 7/1999 | Ni et al. | |
| 6,632,454 B2 | 10/2003 | Beckert et al. | |
| 7,485,294 B2 | 2/2009 | Bourgeois et al. | |
| 8,048,413 B2 | 11/2011 | Huguet et al. | |
| 8,106,000 B2 | 1/2012 | Huguet et al. | |
| 2001/0051150 A1 | 12/2001 | Ranganathan et al. | |
| 2002/0187134 A1 | 12/2002 | Ranganathan et al. | |
| 2005/0186272 A1 | 8/2005 | Mattern et al. | |
| 2005/0249716 A1 | 11/2005 | Bourgeois et al. | |
| 2006/0210631 A1 | 9/2006 | Patel et al. | |
| 2009/0162339 A1 | 6/2009 | Bourgeois et al. | |

FOREIGN PATENT DOCUMENTS

| | | |
|---|---|---|
| CN | 1326745 A | 12/2001 |
| DE | 2437878 A1 | 2/1976 |
| WO | 0018377 A1 | 4/2000 |
| WO | 0114367 A1 | 3/2001 |
| WO | 02060415 A1 | 8/2002 |
| WO | 03032958 A1 | 4/2003 |
| WO | 03075852 A2 | 9/2003 |
| WO | 03080032 A2 | 10/2003 |
| WO | 03086344 A1 | 10/2003 |
| WO | 03103699 A1 | 12/2003 |
| WO | 2004012509 A1 | 2/2004 |
| WO | 2004012713 A1 | 2/2004 |
| WO | 2004012717 A1 | 2/2004 |
| WO | 2004016248 A2 | 2/2004 |
| WO | 2004035090 A1 | 4/2004 |
| WO | 2004039357 A1 | 5/2004 |
| WO | 2004058226 A1 | 7/2004 |
| WO | 2004103311 A2 | 12/2004 |
| WO | 2005007139 A2 | 1/2005 |
| WO | 2005009381 A2 | 2/2005 |
| WO | 2005055955 A2 | 6/2005 |
| WO | 2006010453 A1 | 2/2006 |
| WO | 2006010457 A2 | 2/2006 |
| WO | 2006061069 A1 | 6/2006 |
| WO | 2006122835 A1 | 11/2006 |

OTHER PUBLICATIONS

Jaber et al., American Journal of Kidney Diseases, 1997, vol. 30, No. 5, Suppl. 4, p. S44-S56.*
Gardiner et al., Gut, 1993, vol. 34, p. 51-55.*
Abdelbary, G., et al., "The preparation of orally disintegrating tablets using a hydrophilic waxy binder", "International Journal of Pharmaceutics", 2004, pp. 423-433, vol. 278.
Bourgeois, S., et al., "In vitro and in vivo evaluation of pectin beads for the colon delivery of beta-lactamases", "Journal of Drug Targeting", Jun. 2005, pp. 277-284, vol. 13, No. 5.
Breitkrutz, J., "Leakage of enteric (Eudragit (R) L)-coated dosage forms in simulated gastric juice in the presence of poly(ethylene glycol)", "Journal of Controlled Release", 2000, pp. 79-88, vol. 67.

(Continued)

*Primary Examiner* — Kade Ariani
(74) *Attorney, Agent, or Firm* — Hultquist, PLLC; David Bradin

(57) ABSTRACT

Compositions which deliver adsorbents, alone or in combination with active drug "degrading molecules," in a site-specific manner to the intestine, and which eliminate or at least lower the concentration of residual unwanted material within the intestine, and methods of treatment using the compositions, are disclosed. The compositions are ideally designed to specifically release the adsorbents in a programmed manner at a specific site of the intestinal tract. Programmed delivery prevents adsorbents from interfering with the normal absorption process of a given molecule after oral absorption, until it reaches the lower part of the small intestine. The compositions can be used to adsorb, and therefore remove, any residual drug, metabolite thereof, or bacterial toxin after oral or parenteral administration which would otherwise cause adverse effects in the lower intestine and/or colon.

39 Claims, 5 Drawing Sheets

OTHER PUBLICATIONS

Cao, N., et al., "Activated Carbon Produced from Charcoal Obtained by Vacuum Pyrolysis of Softwood Bark Residues", "Energy and Fuels", 2001, pp. 1263-1269, vol. 15.

Definition of Coffee Charcoal in the List of German Commission E Monographs (Phytotherapy), "Heilpflanzen-Welt (Accessed on Jul. 15, 2010, www.heilpflanzen-welt.de/buecher/BGA-Commission-E-Monographs/0067.htm)", May 5, 1988.

Definition of Kollidon, "Medical Dictionary Online (www.online-medical-dictionary.org/Kollidon.asp2q=Kollidon)", Dec. 31, 2009.

Denti, E., et al., "Adsorption Charcteristics of Cellulose Acetate Coated Charcoals", "J. Biomed. Mater. Res.", 1975, pp. 143-150, vol. 9.

Gardiner, K., et al., "Adsorbents as antiendotoxin agents in expeimental colitis", "Gut", 1993, pp. 51-55 (Abstract Only), vol. 34, No. 1.

Khalil, S., et al., "The in Vitro Adsorption of Some Antibiotics on Antacids", "Pharmazie", 1976, pp. 105-109, vol. 31.

Kim, Y., et al., "Purification and characterization of an erythromycin esterase from an erythromycin-resistant *Pseudomonas* sp.", "FEMS Microbiology Letters", Apr. 23, 2002, pp. 239-244, vol. 210.

Manes, M., et al., "Easily Swallowed Formulations of Antidote Charcoals", "Clinical Toxicology", 1974, pp. 355-364, vol. 7, No. 4.

Pal, K. et al., "Esterification of Carboxymethylcellulose with Acrylic Acid Targeted Drug Delivery System", "Trends Biomater. Artif. Organs.", Jul. 2005, pp. 12-14, vol. 19, No. 1.

Papaioannou, D., et al., "The role of natural and synthethic zeolites as feed additives on the prevention and/or the treatment of certain farm animal diseases", "Microporous and Mesoporous Materials", Jun. 28, 2005, pp. 161-170, vol. 84.

Ramu, J., et al., "Adsorption of Cholera and Heat-Labile *Escherichia coli* Enterotoxins by Various Adsorbents: an in Vitro Study", "Journal of Food Protection", 1997, pp. 358-362, vol. 60, No. 4.

Reshetnikov, V., "Evaluation of the Adsorption Capacity of Enterosorbents and Related Medicinal Preparations", "Pharmaceutical Chemistry Journal", May 2003, pp. 28-32, vol. 37, No. 5.

Singh, G., et al., "Adsorption Characteristics of Norfloxacin to Pharmaceutical Additives", "Drug Development and Industrial Pharmacy", 1988, pp. 1845-1854, vol. 14, No. 13.

Torre, D., et al., "Ciprofloxacin and Activated Charcoal: Pharmacokinetic Data", "Reviews of Infectious Diseases", Jul.-Aug. 1989, pp. S1015-S1016, vol. 11, No. 5.

Wakerly, Z., et al., "Studies on Amidated Pectins as Potential Carriers in Colonic Drug Delivery", "J. Pharm. Pharmacol.", 1997, pp. 622-625, vol. 49.

Watts, P., et al., "Colonic Drug Delivery", "Drug Development and Industrial Pharmacy", 1997, pp. 893-913, vol. 23, No. 9.

Zhang, Y., et al., "Physical Properties and Compact Analysis of Commonly Used Direct Compression Binders", "AAPS PharmSciTech", 2003, pp. 1-11, vol. 4, No. 4, Article 62.

* cited by examiner

SITE-SPECIFIC INTESTINAL DELIVERY OF ADSORBENTS, ALONE OR IN COMBINATION WITH DEGRADING MOLECULES

CROSS-REFERENCE TO RELATED APPLICATIONS

This application is a continuation of U.S. patent application Ser. No. 11/804,259 filed May 17, 2007 and subsequently issued on Nov. 1, 2011 as U.S. Pat. No. 8,048,413, which in turn claims priority of U.S. Patent Application No. 60/801, 121 filed May 17, 2006. The disclosures of all such applications are hereby incorporated herein by reference in their respective entireties, for all purposes.

BACKGROUND OF THE INVENTION

When antibiotics are orally administered, they are usually absorbed by the host in the upper parts of the intestinal tract, such as the duodenum or the jejunum. If the administered dose is not completely adsorbed, it travels further along the intestinal tract, through the ileum and the colon. The portion of the dose that is absorbed reaches the blood stream and, depending on the particular pharmacokinetics of the antibiotic, is excreted through the liver through the bile and back in the intestinal tract in either an active form or an inactive form, depending on the metabolism that has occurred in the liver.

The active metabolites reach the ileum and the colon around the same time as the portion of the antibiotic dose that has not been absorbed, as described above. When antibiotics are administered parenterally, part of the administered dose can, however, reach the intestinal tract through biliary excretion, just as the absorbed fraction of an antibiotic administered orally. Whether the antibiotics have been administered orally or parenterally, there is thus a noticeable fraction of the administered dose that reaches the colon in an active form, where it comes into contact with the numerous commensal bacterial populations within the colon of all living species.

The result is the production of commensal bacteria that are resistant to the antibiotic administered and, often, to many other antibiotics, because the resistance mechanisms to various antibiotics are often physically linked on genetic elements such as plasmids and integrons and thus can be selected by a single antibiotic pressure.

As a result of this process, the patient, or the animal, that has received the antibiotic treatment becomes highly colonized by antibiotic-resistant bacteria, and this can result in further infection by resistant bacteria, and the dissemination of such resistant bacteria in the environment. It is now widely accepted that the selection and dissemination of such resistant bacteria is a major factor that speeds up the dissemination of bacterial resistance to antibiotics both in the community and in the hospitals. Levels of bacterial resistance are currently extremely high, and this is a major public health problem worldwide that could lead to major outbreaks of infections very difficult to treat with available antibiotics either in humans or in animals.

Besides producing antibiotic-resistant bacteria, antibiotics that reach the colon in active form will also profoundly alter the composition of the commensal flora and kill the susceptible species. Among those are often present anaerobic bacteria that have a major physiological role in the intestine of normal subjects and animals, i.e. that of preventing colonization by exogenous potentially pathogenic microorganisms such as *Clostridium difficile* and/or *Candida* sp, and/or multiresistant exogenous bacteria such as Vancomycin-resistant enterococci. Thus, resistance to colonization by such potential pathogens is often reduced during antibiotic treatments. This can lead to the appearance of pathologic signs and symptoms, such as post-antibiotic diarrhea or the more severe forms of pseudomembranous colitis, *Candida* genital infections, particularly in women, or antibiotic-resistant systemic infections in hospitalized patients, particularly patients in intensive care.

In the past, there have been two different approaches, specific and general, for reducing the above mentioned effects of antibiotics on the colonic flora during treatments. A specific approach has been to use enzymes that specifically destroy residual antibiotics in the lower part of the intestine before they can alter the colonic microflora of the treated subjects. This approach is described, for example, in U.S. Application Publication Number 2005/0249716, and can prevent the deleterious effects of beta-lactam antibiotics as well as other antibiotic families, such as the macrolides and the quinolones. A potential limitation of this approach is that the required enzymes or combination of enzymes are sometimes difficult and expensive to produce on large scales, and are only active against a selected class of antibiotic molecules, often against only some of the representatives of this class. That is, the enzymes can inhibit some beta-lactams, or some macrolides, but not all of them. Also, since enzymes are proteins, they tend to be labile, difficult to formulate, and rapidly degraded in the upper part of the intestinal tract by the proteolytic activity found in normal intestinal juices.

It can further be important that the enzymes are not released too early in the intestine, or they will degrade antibiotics before they are significantly absorbed, potentially leading to a decreased activity of the antibiotic treatment. Along a similar line, there have been warnings that the administration of adsorbent materials, such as charcoal, at the same time as antibiotics, can also lead to a decreased efficacy of the antibiotic treatments.

It is worthy of note that antibiotic use in farm animals by far exceeds that in humans, and is a major driving force in the general evolution and dissemination of bacterial resistance to antibiotics.

It would be advantageous to provide additional compositions and methods of treatment for removing excess antibiotics and their metabolites from the intestinal tract, in order to reduce undesirable side effects such as diarrhea and the development of antibacterial-resistant bacteria without changing the fate of absorption on the antibiotic and its potential to treat the infection for which it had been administered. The present invention provides such compositions and methods of treatment.

SUMMARY OF THE INVENTION

The present invention is directed to compositions and methods of treatment, which use adsorbents, alone or in combination with active "drug degrading molecules", ideally delivered in a site-specific intestinal delivery system, to eliminate or at least lower the concentration of residual unwanted material within the intestine. The material can be, for example, residual active antibiotics, metabolites, and bacterial or other toxins. However, the adsorbents can also reduce the concentration of other compounds as well, including drugs which have a beneficial side effect in the body other than in the gastrointestinal tract, but cause side effects in the gastrointestinal tract.

These adsorbents, or combinations thereof, can be formulated in capsules, tablets or any acceptable pharmaceutical composition, and are ideally designed to specifically release the adsorbents in a programmed manner at a specific site of the intestinal tract. The programmed delivery prevents adsorbents from interfering with the normal absorption process of a given molecule after oral absorption, until it reaches the lower part of the small intestine, i.e. the ileum, and the colon. In one embodiment, the compositions allow the formulated adsorbents to recover their maximum adsorption capabilities when they reach the desired part of the intestinal tract.

The compositions can be used to adsorb, and therefore remove from the intestine, any residual drug, or metabolite thereof after oral or parenteral administration of an active drug, or bacterial toxin, which would otherwise cause adverse effects in the hosts when they reach the lower intestine and/or colon.

Active drugs of interest include antibiotics of any family such as beta-lactams, cyclines, macrolides, quinolones, glycopeptides, and so forth or any other molecule or toxin that could have serious adverse effects on the intestinal tract, such as, but not limited to bacterial toxins, and small molecules.

In one embodiment, the compositions are substantially devoid of pectin. The term "substantially devoid" means that there is not sufficient pectin, in this embodiment, to result in pectin participating in the activity or delivery mechanism of the composition.

To reduce the concentration of antibiotics, or other molecules with local adverse effects on the intestine, it can be important to release the adsorbent at the earliest possible time after the absorption of the antibiotic is complete, with rapid release being preferred. The dosage of the adsorbent is ideally selected to be sufficient to significantly reduce the concentration of the unwanted chemical in the intestine, and also such that the adsorbent remains effective when released. Representative dosage forms include capsules, tablets and other suitable dosage forms which provide a relatively rapid effect on the removal of antibiotic activity in the colon.

In some embodiments, it can be desirable to release the adsorbents in the colon. However, the portion of the intestine where antibiotics are absorbed, following oral administration, is the upper part of the small intestine, that is, the duodenum and the first part of the jejunum, not the ileum. Indeed, absorption of most antibiotics is complete within four hours in humans. Thus, in some embodiments, the adsorbing activity of the adsorbents occurs before the colon, in the lower part of the small intestine, i.e. the ileum. In that case, the absorption of the antibiotic in the upper part of the intestinal tract would not be affected (and thus the primary effect of the antibiotic treatment would remain unchanged), but the antibiotic residues (either the part not absorbed after oral absorption and that excreted through the biliary canal or intestinal secretion after oral or parenteral administration) would be readily adsorbed and inactivated even before they reach the ileo-cecal valve and the colon.

This provides a major and very innovative advantage over the above-mentioned general and specific approaches. Conceptually, whereas the prior art approaches were designed to provide colonic delivery of an enzyme to inactivate antibiotics, the present compositions provide programmed delivery of the adsorbent (alone or in combination with an enzyme) to take advantage of the window that exists between the part of the intestine where the antibiotics are absorbed and that where their deleterious effects on the commensal bacteria occur.

Technically, the compositions are very simple and robust, and as such will be relatively inexpensive to implement both in human and animal applications.

BRIEF DESCRIPTION OF THE FIGURES

In FIG. 1, the concentration of ciprofloxacin is 75 µg/ml in 50 ml of simulated colonic medium (SCM, pH 6.4); blue diamonds represent cholestyramine at a concentration of 75 µg/ml, red squares represent sevelamer chlorhydrate at a concentration of 75 µg/ml, and yellow triangles represent activated charcoal at a concentration of 75 µg/ml.

In FIG. 2, the concentration of ciprofloxacin is 75 µg/ml in 50 ml of simulated colonic medium (pH 6.4); blue diamonds represent cholestyramine at a concentration of 180 µg/ml, red squares represent sevelamer chlorhydrate at a concentration of 180 µg/ml, and yellow triangles represent activated charcoal at a concentration of 180 µg/ml.

DETAILED DESCRIPTION

Figure 1:
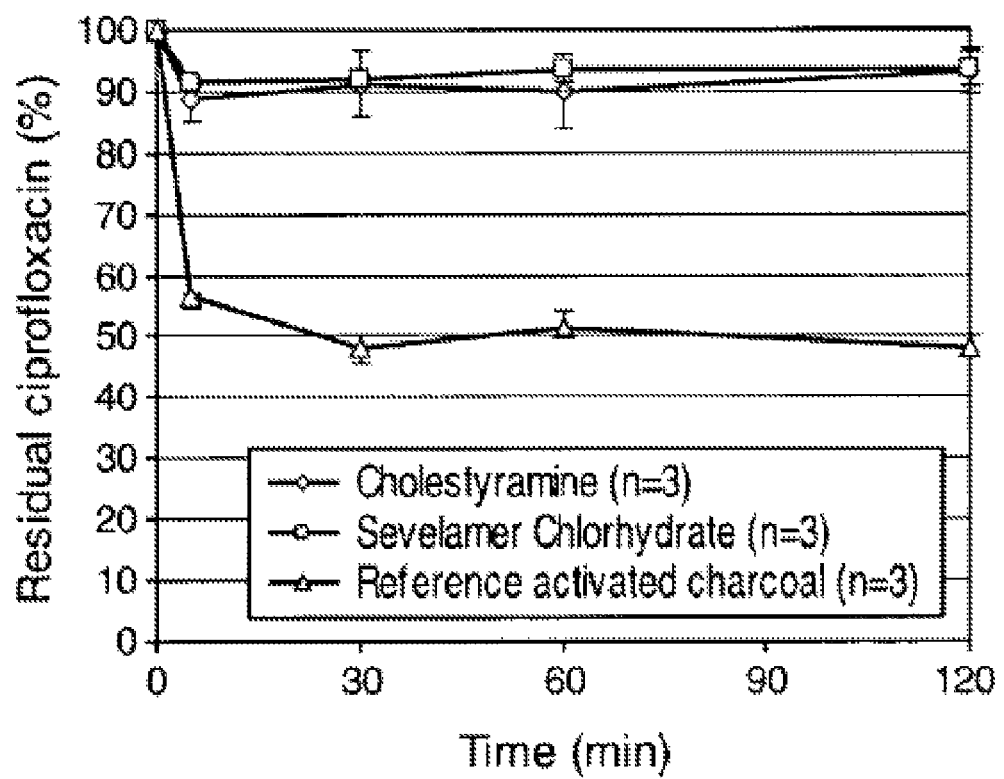
FIGS. 1 and 2 present the kinetics of ciprofloxacin removal with cholestyramine, sevelamer chlorhydrate and activated charcoal in simulated colonic medium (SCM), pH 6.4.

The delivery systems including the adsorbents, and methods of preparation and use thereof, are described in more detail below.

I. Components of the Adsorbent-Containing Delivery System

The adsorbent can be formulated from techniques known to those of skill in the art, and as described below in detail. The delivery forms include, but are not limited to, tablets, capsules, granules, inert particles, semi-solid forms, and the like. These delivery systems can be subsequently coated, using known techniques, to provide protection from gastric fluid and to provide release of the adsorbent at the desired site of interest within the intestine.

A. Types of Adsorbents

The adsorbents used to prepare the delivery system typically have a high specific surface, though a reduced pore size is not necessarily unfavorable, as it can help adsorb large molecules, and the adsorbents can be of pharmaceutical grade or not. Examples of suitable adsorbents include activated charcoal, clays, including bentonite, kaolin, montmorillonite, attapulgite, halloysite, laponite, and the like, silica, including colloidal silica (Ludox.® AS-40 for example), mesoporous silica (MCM41), fumed silica, zeolites and the like, talc, cholesteramine and the like, polystyrene sulfonates and the like, mono and polysulfonated resins, and any other resins of interest such as those used for bacteriologic testing such as BACTEC® resins. Among these adsorbents, it can be preferred to use those of pharmaceutical grade, such as activated charcoal USP (Merck, France or other sources such as Norit), kaolin (VWR, France), attapulgite (Lavollee, France), bentonite (Acros Organics, France), Talc USP (VWR, France).

The amount of adsorbent to produce a single dosage form will vary depending upon the host being treated, the particular mode of administration. The amount of adsorbent to produce a single dosage form will generally be that amount of the compound which produces a therapeutic effect. The therapeutic effects include providing a therapeutically significant decrease in the amount of the antibiotic, metabolite thereof, bacterial toxin, or other compound which causes adverse effects in the colon, relative to when the composition is not administered.

Generally, out of one hundred weight percent of the composition, the proportion of the adsorbent will range from about 1 percent to about ninety-nine percent, preferably from about 5 percent to about 70 percent, most preferably from about 10 percent to about 50 percent.

B. Optional Additional Components

The delivery system can optionally include one or more additional components. Ideally, these are components that are not significantly adsorbed by the adsorbent or, when adsorbed, remain fully active, and include excipients or enzymes which inactivate antibiotics or other substances. For example, the enzymes can be enzymes which inactivate beta-lactams, quinolones, cyclines, glycopeptides macrolides and/or other antibiotics, such as beta-lactamases or erythromycin esterases. While not wishing to be bound to a particular theory, it is believed that the adsorbent could help protecting the enzyme from degradation and bring the antibiotic in close contact with the enzyme, further assisting with the removal of the active antibiotic from the colon of the patient.

The amount of enzyme necessary to degrade the antibiotic in the intestine will be expected to vary with the dosage of the antibiotic, the type of enzyme, the patient weight, the severity of the infection, and other factors. However, the enzymes can be, and ideally are administered in excess, based on an estimate of the potential maximal residual dose, so that there will always be an excess of the enzyme relative to the amount of antibiotic.

C. Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions can be specially formulated for administration in solid or liquid form.

The phrase "therapeutically-effective amount" as used herein means that amount of one or more of the compounds described above, material, or composition comprising one or more of the compounds described above which is effective for producing some desired therapeutic effect.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a solid filler, diluent, excipient involved in carrying or transporting the subject compound from one organ, or portion of the body, to another organ, or portion of the body. Each carrier must be "acceptable" in the sense of being compatible with the other ingredients of the formulation and not injurious to the patient.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the present invention include those suitable for oral administration. The formulations can conveniently be presented in unit dosage form and can be prepared by any methods well known in the art of pharmacy.

Formulations of the invention suitable for oral administration can be in the form of capsules, dragees, troches, cachets, pills, tablets, powders, granules, or as a suspension in an aqueous or non-aqueous liquid, each containing a predetermined amount of an adsorbent or a combination of adsorbent and enzyme as an active ingredient.

In solid dosage forms of the invention for oral administration (capsules, tablets, pills, dragees, powders, granules and the like), the active ingredient is mixed with one or more pharmaceutically-acceptable carriers, such as (1) fillers or extenders, such as starches, lactose, sucrose, glucose, mannitol, and/or silicic acid; (2) binders, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, starch, (5) wetting agents, such as, for example, cetyl alcohol, glycerol monostearate, and non-ionic surfactants; (6) lubricants, such a talc, calcium stearate, magnesium stearate, solid polyethylene glycols, sodium lauryl sulfate, and mixtures thereof; and, optionally, (10) coloring agents. In the case of capsules, tablets and pills, the pharmaceutical compositions can also comprise buffering agents. Solid compositions of a similar type can also be employed as fillers in soft and hard-shelled capsules using such excipients as lactose or milk sugars, as well as high molecular weight polyethylene glycols and the like.

A tablet can be made by compression or molding, optionally with one or more accessory ingredients. Compressed tablets can be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets can be made by molding in a suitable machine a mixture of the powdered compound moistened with an inert liquid diluent.

The tablets, and other solid dosage forms of the pharmaceutical compositions of the present invention, such as tablets, capsules, pills and granules, can optionally be prepared with coatings and shells, such as gastro-resistant coatings and/or complementary enteric coatings to provide release of the adsorbent in a certain portion of the gastrointestinal tract and other coatings well known in the pharmaceutical-formulating art.

Examples of embedding compositions which can be used include polymeric substances and waxes. The active ingredient can also be in micro-encapsulated form, if appropriate, with one or more of the above-described excipients.

The systems with different drug release mechanisms described above can be combined in a final dosage form comprising single or multiple units. Examples of multiple units include multilayer tablets, capsules containing tablets, beads, granules, etc.

Delayed release formulations are created by coating a solid dosage form with a film of a polymer which is insoluble in the acid environment of the stomach, and soluble in the neutral environment of the small intestines and/or colon.

The delayed release dosage units can be prepared, for example, by coating the delivery system with a selected coating material. The drug-containing composition can be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and can be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon.

Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit®. (Degussa AG, Dusseldorf, Germany), including Eudragit® L30D-55 and L100-55 (soluble at pH 5.5 and above), Eudragit® L-100 (soluble at pH 6.0 and above), Eudragit® (soluble at pH 7.0 and above, as a result of a higher degree of esterification), Eudragits® NE, RL and RS (water-insoluble polymers having different degrees of permeability and expandability) and Eudragit FS30D a tercopolymer of methacrylic acid, methyl acrylate and methylmethacrylate; vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials can also be used. Multi-layer coatings using different polymers can also be applied. The preferred coating weights for particular coating materials can be readily determined by those skilled in the art by evaluating individual release profiles for tablets, beads and granules prepared with different quantities of various coating materials. It is the combination of materials, method and form of application that produce the desired release characteristics, which can be determined by those of skill in the art, considering the nature of the compound to be adsorbed, as well as other relevant factorssui.

The coating composition can include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates can also be used. Pigments such as titanium dioxide can also be used. Small quantities of an anti-foaming agent, such as a silicone (e.g., simethicone), can also be added to the coating composition.

Alternatively, a delayed release tablet can be formulated by dispersing the drug within a matrix of a suitable material such as a hydrophilic polymer or a fatty compound. The hydrophilic polymers can be comprised of polymers or copolymers of cellulose, cellulose ester, acrylic acid, methacrylic acid, methyl acrylate, ethyl acrylate, and vinyl or enzymatically degradable polymers or copolymers as described above. These hydrophilic polymers are particularly useful for providing a delayed release matrix. Fatty compounds for use as a matrix material include, but are not limited to, waxes (e.g. carnauba wax) and glycerol tristearate. Once the active ingredient is mixed with the matrix material, the mixture can be compressed into tablets.

These dosage forms can be administered to humans and other animals for therapy by any suitable route of administration, but ideally a route that delivers the dosage forms to the intestine, and preferably via the oral route.

Actual dosage levels of the active ingredients in the pharmaceutical compositions of this invention can be varied so as to obtain an effective removal of any residual antibiotic or chemical or toxin in the intestinal tract, for a particular patient, composition, and mode of administration, without being toxic to the patient.

The selected dosage level will depend upon a variety of factors including the activity of the particular compound of the present invention employed, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the pharmaceutical composition at levels lower than that required in order to achieve the desired therapeutic effect and gradually increase the dosage until the desired effect is achieved.

In general, a suitable daily dose of composition will be that amount of the composition which is the lowest dose effective to produce a therapeutic effect. Such an effective dose will generally depend upon the factors described above.

If desired, the effective daily dose of the active compound (i.e., the adsorbent and, optionally, an enzyme or other compound present in the composition) can be administered as two, three, four, five, six or more sub-doses administered separately at appropriate intervals throughout the day, optionally, in unit dosage forms.

The compounds according to the invention can be formulated for administration in any convenient way for use in human or veterinary medicine, by analogy with other pharmaceuticals.

The term "treatment" is intended to encompass also prophylaxis, therapy and cure.

The patient receiving this treatment can be any animal in need, including primates, in particular humans, and other mammals such as equines, cattle, swine and sheep; and poultry and pets in general.

The addition of the composition to animal feed is preferably accomplished by preparing an appropriate feed premix containing the active compound in an effective amount and incorporating the premix into the complete ration.

In one embodiment, the invention relates to the use of at least one of attapulgite, kaolin, and activated charcoal, for adsorbing at least one antibiotic (including, but not limited to, to ciprofloxacin or amoxicillin), in particular in the intestinal tract, and preferably in one embodiment before the colon part, and in another embodiment, in the colon.

Preferably, the attapulgite, kaolin, activated charcoal, or one of their combinations is delivered between the part of the intestine where the antibiotics are absorbed (duodenum and jejunum) and that where their deleterious effect on the commensal bacteria occur (the colon).

II. Methods of Treatment Using the Drug Delivery Devices

The drug delivery devices can be used to treat those types of conditions and disorders for which intestinal delivery of adsorbents is appropriate. In one embodiment, the disorders are those that result from exposure of the colon to antibiotics, such as diarrhea. In this embodiment, the adsorbents inactivate antibiotics, and the devices can be administered in a therapeutically effective dosage to a patient who has been, is being, or will be administered an antibiotic. Any antibiotic that can be adsorbed into/onto the adsorbent can be inactivated. Representative examples of antibiotic classes that can be adsorbed include beta-lactams, cyclines, macrolides, quinolones, aminoglycosides, glycopeptides, sulfamides, phenicols, sulfamides, furans, polypeptides, oxazolidones and antibiotics such as fosfomycin, rifampin and the like.

In another embodiment, the drug delivery devices are administered to a patient who suffers from the effects of bacterial or fungal toxins on the colon. Examples of such toxins include mycotoxins, endotoxins or enterotoxins, such as those produced by *Clostridium difficile* (believed to be a major cause of post-antibiotic diarrhea and pseudomembranous colitis throughout the world). In this embodiment, the adsorbents are administered in a therapeutically effective dosage to adsorb the toxins.

In another embodiment, the drug delivery devices are administered to a patient who suffers from a disorder treated with pharmaceutically active agents which bind to or interact with relevant targets in the body of the patient other than in the colon to treat the disorder, but which, when they bind to or interact with targets in the colon, result in side effects. Representative targets include, for example, receptors and enzymes, for example, cholinergic and serotonin receptors. For example, the colon includes cholinergic (Iino and Nojyo, Neuroscience, 138(2):549-559 (2006)) and serotonin receptors, which are also present in the central nervous system. Treatment with agents that bind to cholinergic receptors can result in side effects if the compounds bind to receptors in the colon. Co-administration of the adsorbent delivery system described herein and the agents that bind to such receptors can minimize or eliminate these side effects.

It is known that gastrointestinal problems are commonly reported because of adverse drug reactions with blood pressure medications (Calcium Channel blockers), pain medications (especially narcotics), antidepressants, antacids that contain aluminum and calcium, anti-Parkinson drugs, antispasmodics, diuretics, and anticonvulsants, and that many drug classes are associated with constipation. Often times, constipation persists, and patients discontinue treatment because the side effect is burdensome. Drugs such as risperidone can be associated with colonic disorders, such as megacolon (Lim and Mahendron, Singapore Med. J., 43(10):530-532 (2002).

The invention further relates to the use of an intestinal and or colonic delivery system for manufacturing a pharmaceutical composition for treating or preventing at least one of the above conditions.

The present invention will be further understood with reference to the following non-limiting examples.

EXAMPLE 1

Adsorption Efficiency in Simulated Colonic Conditions with Unformulated Adsorbents In early works (see for example, PCT application No. PCT/EP2006/005629, the contents of which are hereby incorporated by reference), adsorption of amoxicillin and ciprofloxacin by three pharmaceutical grade adsorbents (activated charcoal, attapulgite and kaolin) was tested under simulated colonic conditions by determining residual concentration of antibiotics using HPLC. The simulated colonic medium (SCM) used for these experiments was a solution made of HEPES (2.383 g/L) and NaCl (8.474 g/L) adjusted to pH 6. Adsorbents were incubated in SCM at 37° C. under gentle tangential stirring. At desired time points, suspensions were collected and centrifuged at 10,000 RPM using a microcentrifuge. The supernatant was filtered on a syringe driven filter unit (Millex®-HV, 0.45 PVDF, 4 mm; Millipore, France) and assayed for their antibiotic concentration using HPLC. Control samples containing, or not containing, antibiotics in SCM were incubated under the same experimental conditions in the absence of adsorbents. The proportion (%) of antibiotics remaining in SCM after incubation with adsorbents was determined by comparison with those positive and negative controls.

Adsorption Kinetics of Amoxicillin

The capacity of attapulgite, activated charcoal and kaolin to adsorb amoxicillin in simulated colonic conditions was studied. The concentration of amoxicillin before and after exposure to the adsorbents was determined using HPLC coupled with UV detection ($\lambda=230$ nm), as described in PCT application No. PCT/EP2006/005629.

The results of this work demonstrated that amoxicillin adsorption was very efficient with activated charcoal, whereas it was observed to a lesser degree with attapulgite and kaolin. After 6 hours of incubation, the percentage of amoxicillin eliminated by the different adsorbents varied from around 25% to up to 95% with a greater reduction for activated charcoal. These results showed that the maximum of adsorption is always reached after a relatively short contact time with activated charcoal. Adsorption of amoxicillin on charcoal (10 mg/ml SCM) reached saturation after 15 to 30 min of incubation. Attapulgite and kaolin were able to reduce amoxicillin concentration of the solution, but only with high amounts of adsorbent amounts (200 mg/mL) and the steady state was only reached after 6 hours.

Adsorption Kinetics of Ciprofloxacin

The concentration of ciprofloxacin remaining in the solution after contact with unformulated adsorbents was determined using HPLC coupled with UV detection at 278 nm, as described in the reference document: PCT application No. PCT/EP2006/005629. Control samples were prepared as mentioned above.

In comparison with amoxicillin, ciprofloxacin was adsorbed faster by all three adsorbents tested, the plateau being reached between 15 and 30 minutes in all cases. Activated charcoal exhibited a higher adsorption capacity than attapulgite, which was more efficient than kaolin.

EXAMPLE 2

Comparison of the Adsorption of Ciprofloxacin by Synthetic Resins and Activated Charcoal The capacity of two commercially available synthetic resins to adsorb ciprofloxacin in simulated colonic conditions was compared to that of activated charcoal. The two resins tested were ionic exchange resins, cholestyramine (Sigma-Aldrich, France) and sevelamer chlorhydrate (Renagel®, Genzyme, USA), that are generally used to treat complications of renal failures. The pharmaceutical grade activated charcoal was from Norit (Belgium). The simulated colonic medium (SCM) used for these experiments was a solution made of HEPES (2.383 g/L) and NaCl (8.474 g/L) adjusted to pH 6.4.

3.75 mg or 9 mg of the synthetic resins or the activated charcoal were incubated in 50 ml of the colonic medium containing 3.75 mg of ciprofloxacin at 37° C. under gentle tangential stirring. At desired time points, aliquots of the suspensions were collected and centrifuged 5 min at 13,000 RPM using a micro-centrifuge. The supernatant was filtered on a syringe-driven filter unit (Millex®-HV, 0.45 μm, PVDF, 4 mm; Millipore, France) and assayed for their antibiotic concentration using HPLC coupled with UV detection at 278 nm. The separation was achieved at 25° C., using a C18 Symmetry® column (5 μm, 150.times.4.6 mm; Waters, France). The mobile phase was 10% acetonitrile in 0.02 M $NaH_2PO_4$ (adjusted to pH 3 with orthophosphoric acid). The flow rate was 1 mL/min. Control samples of SCM containing or not ciprofloxacin were incubated under the same experimental conditions. The percentage of antibiotic remaining in the SCM after incubation with adsorbents was determined by comparison with positive and negative controls.

Figure 2:
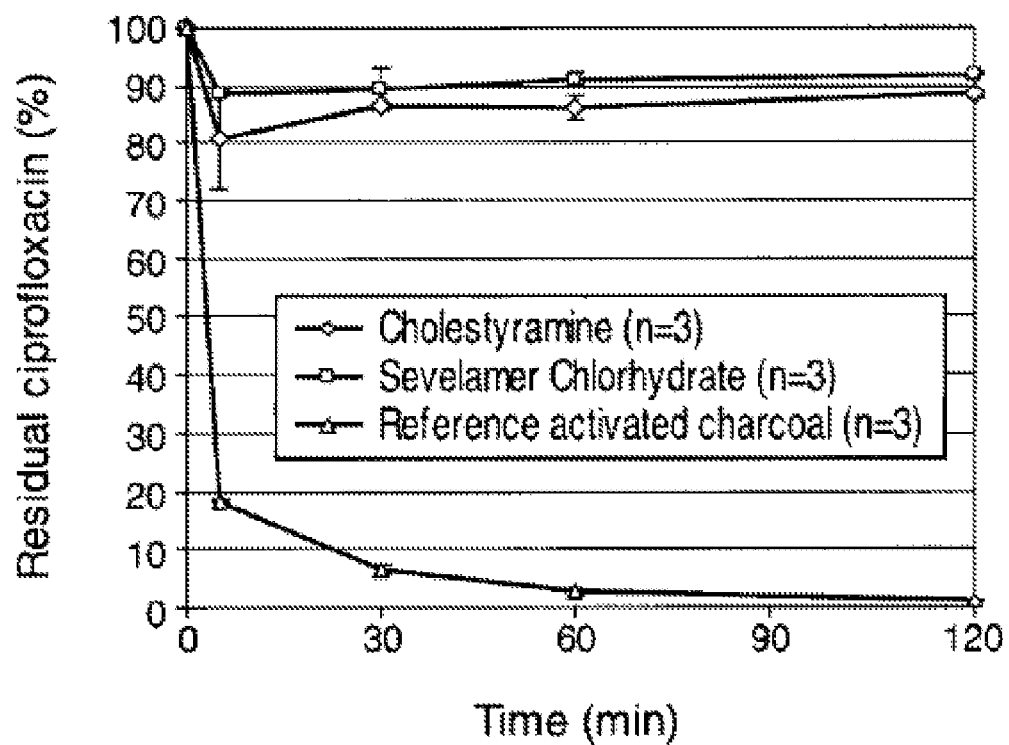

FIGS. 1 and 2 compare the proportion of residual ciprofloxacin as a function of incubation time with the different adsorbents using weight/weight ratios of adsorbents to ciprofloxacin of 1 and 2.4 respectively. The results presented in FIGS. 1 and 2 demonstrate that activated charcoal exhibits a higher adsorption capacity than cholestyramine and sevelamer chlorhydrate, whatever the weight ratio tested. As observed in FIG. 2, activated charcoal removes all of the ciprofloxacin contained in the simulated colonic medium (pH 6.4) after 60 min of incubation, when it is used at a charcoal to antibiotic (weight/weight) ratio of 2.4.

EXAMPLE 3

Adsorption of Antibiotics by Various Activated Charcoals

The adsorption of ampicillin, amoxicillin and ciprofloxacin was tested with various activated charcoals from different origins with distinct physical and chemical characteristics in simulated colonic conditions. Table 1 below shows the physical and chemical characteristics of seven pharmaceutical grade charcoals from different manufacturers.

TABLE 1 physicochemical characteristics of pharmaceutical grade charcoals from various manufacturers.

| Manufacturer | Reference | Specific surface ($m^2/g$) | Porous volume (mL/g) | Point of Zero Charge (pH) | Surface acidic function (meq/g) | Density Apparent | Density Real |
|---|---|---|---|---|---|---|---|
| Norit | CC15 | 1803 | 0.95 | 4.36 | 29.7 | 0.25 | 2.49 |
| Norit | CC16 | 1663 | 0.80 | 3.47 | 25.1 | 0.29 | 2.36 |
| Norit | CC17 | 1521 | 0.90 | 3.53 | 26.2 | 0.23 | 2.34 |
| Hänseler | CC18 | 1674 | 0.65 | 5.71 | 16.1 | 0.27 | 1.94 |
| Merck | CC19 | 1517 | 0.85 | 3.42 | 28.5 | 0.22 | 1.95 |
| Prolabo | CC20 | 1312 | 0.55 | 3.88 | 22.5 | 0.31 | 1.99 |
| Certa | CC21 | 1419 | 0.85 | 3.17 | 27.9 | 0.25 | 2.07 |

The proportion of ampicillin, amoxicillin or ciprofloxacin adsorbed after 60 min of incubation onto the seven pharmaceutical grade activated charcoals described above was determined in a simulated colonic medium (SCM solution made of HEPES (2.383 g/L) and NaCl (8.474 g/L) adjusted to pH 6.4.

Briefly, 50 mg of the different charcoals were incubated with 250 mg of ampicillin in 50 ml of SCM (pH 6.4) under gentle stirring (i.e. 1 mg/ml of a suspension of activated charcoal with 5 mg/ml ampicillin in SCM pH 6.4). 98 mg of the different charcoals were incubated with 125 mg of amoxicillin in 50 ml of SCM, pH 6.4 under gentle stirring (i.e. 1.96 mg/ml of a suspension of activated charcoal with 2.5 mg/ml amoxicillin in SCM pH 6.4).

3 mg of the different charcoals were incubated with 3.75 mg of ciprofloxacin in 50 ml of SCM, pH 6.4 under gentle stirring (i.e. 60 μg/ml of a suspension of activated charcoal with 75 μg/ml ciprofloxacin in SCM pH 6.4).

After 60 min of incubation, aliquots of the suspensions were collected and centrifuged 5 min at 13 000 RPM using a micro-centrifuge. The supernatant was filtered on a syringe driven filter unit (Millex®-HV, 0.451 PVDF, 4 mm; Millipore, France) and assayed for their antibiotic concentration using HPLC coupled with UV detection. Control samples of SCM containing or not antibiotics were incubated under the same experimental conditions. The percentage of antibiotics remaining in the SCM after incubation with adsorbents was determined by comparison with those positive and negative controls.

Table 2 shows the results of the adsorption of ampicillin by activated charcoal using a weight/weight ratio of charcoal to antibiotic of 0.2. Comparison of the results obtained with the different charcoals for the adsorbtion of ampicillin demonstrated that the best results were obtained with charcoals CC15 and CC18 (from Norit and Hanseler, respectively).

These two adsorbents were further tested for their capacity to adsorb amoxicillin and ciprofloxacin in simulated colonic conditions. Table 2 shows the percentage of each antibiotic adsorbed using weight/weight ratios of charcoal to each of these two antibiotics of 0.8.

TABLE 2 percentage of ampicillin, amoxicillin or ciprofloxacin adsorbed by pharmaceutical grade charcoals from different manufacturers, after 60 min of incubation in simulated colonic medium, pH 6.4.

| | Charcoal | | | | | | | Charcoal/ |
| --- | --- | --- | --- | --- | --- | --- | --- | --- |
| | CC 19 | CC 20 | CC 21 | CC 17 | CC 16 | CC 18 | CC 15 | Antibiotic ratio |
| % of eliminated Ampicillim | 8.1 | 9.4 | 9.5 | 9.9 | 11.1 | 12 | 12.2 | 0.2 |
| % of eliminated Amoxicillin | ND* | ND | ND | ND | ND | 36.2 | 38.9 | 0.8 |
| % of eliminated Ciprofloxacin | ND | ND | ND | ND | ND | 39.2 | 47.1 | 0.8 |

*not determined

EXAMPLE 4

Adsorption of Amoxicillin and Ciprofloxacin by Different Amounts of Selected Activated Charcoals The adsorption of amoxicillin and ciprofloxacin by different quantities of CC15 or CC18 activated charcoals was measured in order to determine the weight/weight ratio of charcoal to antibiotics that leads to total elimination of the antibiotics in simulated colonic medium.

The percentage of eliminated amoxicillin or ciprofloxacin was determined after 60 min of incubation with different amounts of CC15 or CC18 charcoals (weight/weight ratios 0.8, 2.4 or 20), in a simulated colonic medium (SCM solution made of HEPES (2.383 g/L) and NaCl (8.474 g/L) adjusted to pH 6.4). Briefly, 50 ml of simulated colonic medium (pH 6.4) containing 2.5 mg/ml amoxicillin was incubated with CC15 or CC18 charcoals at concentrations of 2 mg/ml (weight/weight ratio 0.8), 6 mg/ml (weight/weight ratio 2.4) or 7.5 mg/ml (weight/weight ratio 3).

Alternatively, 50 ml of SCM (pH 6.4) containing 75 µg/ml ciprofloxacin was incubated with CC15 or CC18 charcoals at 60 µg/ml (weight/weight ratio 0.8), 180 µg/ml (weight/weight ratio 2.4) or 1.5 mg/ml (weight/weight ratio 20).

After 60 min of incubation, aliquots of the suspensions were collected and centrifuged 5 min at 13 000 RPM using a micro-centrifuge. The supernatant was filtered on a syringe driven filter unit (Millex®-HV, 0.45 µm, PVDF, 4 mm; Millipore, France) and assayed for their antibiotic concentration using HPLC coupled with UV detection. Control samples of SCM containing, or not containing, antibiotics were incubated under the same experimental conditions. The percentage of antibiotics remaining in the SCM after incubation with adsorbents was determined by comparison with those positive and negative controls.

Figure 3:
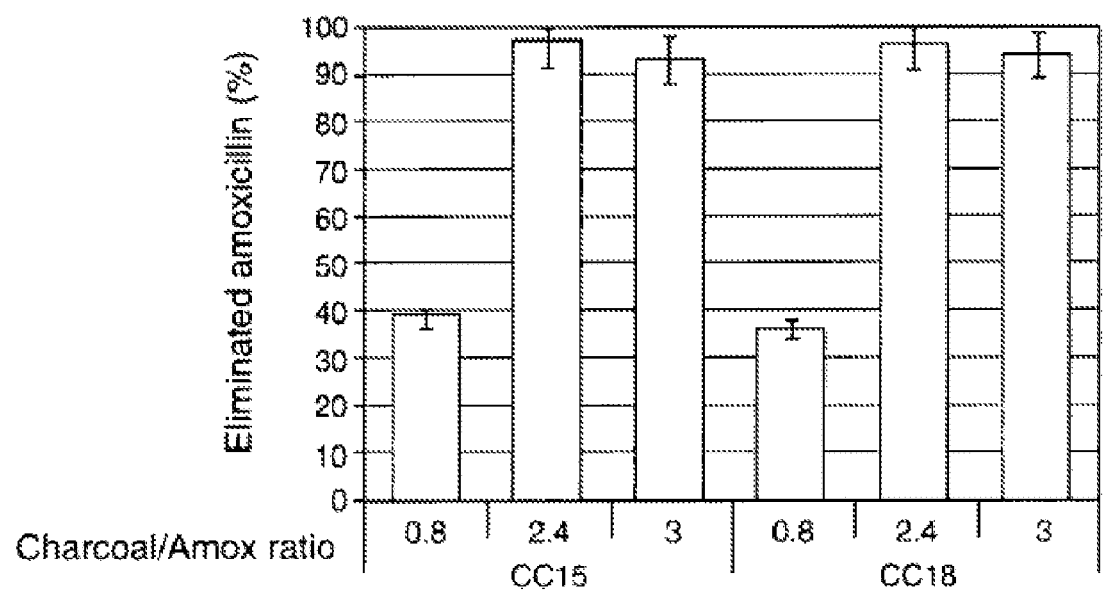
FIG. 3 presents the proportion of amoxicillin (initial concentration of 2.5 mg/ml in 50 ml of simulated colonic medium, pH 6.4) eliminated after 60 min of incubation with CC15 or CC18 charcoals. The concentrations of the charcoals in 50 ml of the simulated colonic medium are 2 mg/ml, 6 mg/ml or 7 mg/ml, for ratios charcoals to amoxicillin of 0.8, 2.4 or 3, respectively.
Figure 4:
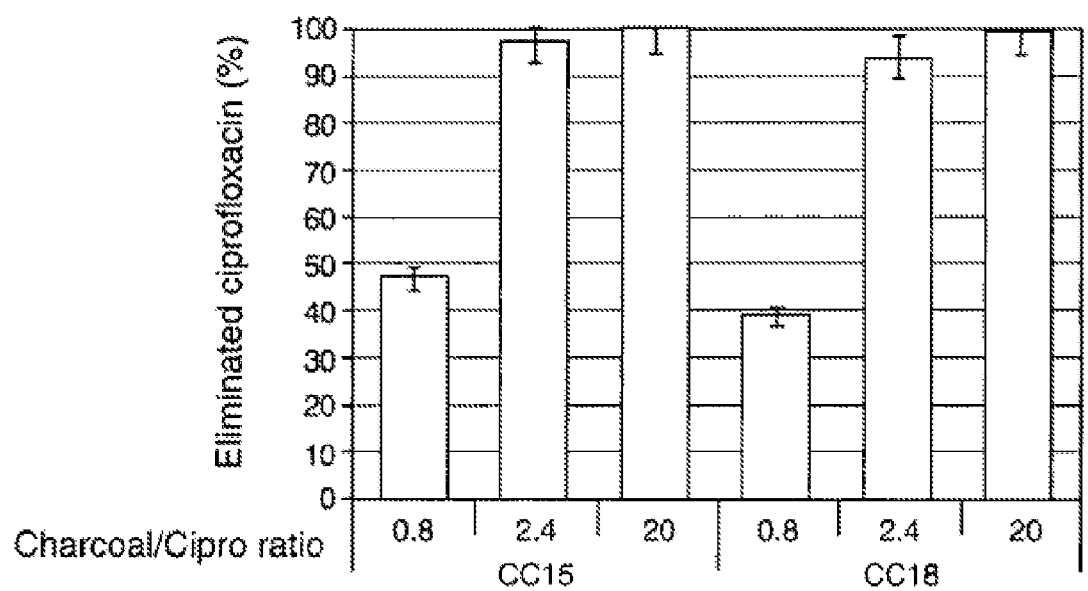
FIG. 4 presents the proportion of ciprofloxacin (initial concentration 75 µg/ml in 50 ml of simulated colonic medium, pH 6.4) eliminated after 60 min of incubation with CC15 or CC18 charcoals. The concentrations of the charcoals in 50 ml of the simulated colonic medium are 60 µg/ml, 180 µg/ml or 1.5 mg/ml, for weight/weight ratios of charcoals to ciprofloxacin of 0.8, 2.4 and 20, respectively.

The results presented in FIGS. 3 and 4 show that at a weight/weight ratio of activated charcoal to antibiotics of 2.4 and above, both CC15 and CC18 charcoals were able to adsorb more than 90% of amoxicillin and ciprofloxacin.

EXAMPLE 5

Pharmaceutical Formulation

The feasibility of an oral dosage form for the programmed and the site specific delivery of activated charcoal was investigated by testing different pharmaceutical formulation processes. The objective was to develop a galenic form appropriate for the controlled release of activated charcoal in the desired part of the gastrointestinal tract yet preserving as much as possible the adsorption characteristics of the charcoal. Activated charcoal is a very challenging product to formulate because of its physicochemical properties such as low density, hydrophobicity, wetting properties, etc. Attempting to formulate the charcoal for the intended use described in this invention at a therapeutic dose for human administration was not possible using conventional direct compression because of the very low cohesive properties of activated charcoal. Even simple wet granulation and compression lead to tablets exhibiting poor adsorption properties.

It was therefore necessary to increase the relative density of the charcoal, for example, by wet granulation using specific binders (Sorbitol, hydroxypropycellulose, Starch 1500). Cellulose and cellulose derivatives, such as hydroxypropylcellulose (L-HPC, Hercules) and the like, were the most appropriate binders for providing the best mechanical and adsorption properties with the antibiotics tested.

Table 3 shows one example of granules obtained by wet granulation using a Collette GRAL high shear mixer granulator (GRAL10, Collette, Belgium).

TABLE 3 example of a composition for granules obtained by wet granulation

| Composition | Amount (%) |
| --- | --- |
| Activated charcoal (Norit) | 85 |
| L-HPC (Hercules) | 5 |
| Starch 1500 (Colorcon) | 10 |
| | 100% |

These granules can then be introduced into hard capsules, or compressed into tablets, and both forms will be coated with an entero-soluble polymer such as Eudragit® L30D-55 (Degussa, Darmstadt, Germany) for example.

In order to optimize the release of the activated charcoal and to preserve its adsorption capacity, semi-solid formulations were tested by mixing activated charcoal with dispersants that solidify at ambient temperature such as polyethyleneglycol (PEG 300, 400, or 4000), glycerol, etc. . . . . The most appropriate excipient to formulate charcoal in a semi-solid form was PEG 400 (Fagron, Belgium). Table 4 shows one example of semi-solid form prepared by mixing the activated charcoal with PEG 400 in a planetary mixer at 40° C.

TABLE 4 example of a semi-solid composition.

| Composition | Amount (%) |
|---|---|
| Activated charcoal (Norit) | 30 |
| PEG 400 (Fagron) | 70 |
| | 100% |

This semi-solid form can be introduced into soft or hard capsules that can be coated with specific entero-soluble polymers, such as Eudragit® L30D55 (Degussa, Darmstadt, Germany).

Dosage forms that contain multiple units, such as pellets individually coated by entero-soluble polymers such as the one described above, can be preferred in order to improve the in vivo dispersion of the activated charcoal. Such pellets present more practical flexibility, because coating can be directly achieved on their surface using a fluid bed system for example. Two different processes, one-pot pelletization and extrusion-spheronisation, were investigated to obtain such pellets. Production of pellets using a Collette GRAL high shear mixer granulator (GRAL10, Collette, Belgium) offers better pharmacotechnical properties, batch homogeneity and reproducibility than two step processes using extrusion-spheronisation. One example of an appropriate formulation for pelletization of activated charcoal is described in Table 5. TABLE-US-00005 TABLE 5 Example of a composition for pellets using one-pot pelletization. Composition Amount (%) Activated charcoal (Norit) 80 Avicel PH102 (FMC) 15 Kollidon (BASF) 5 100%

Figure 5:
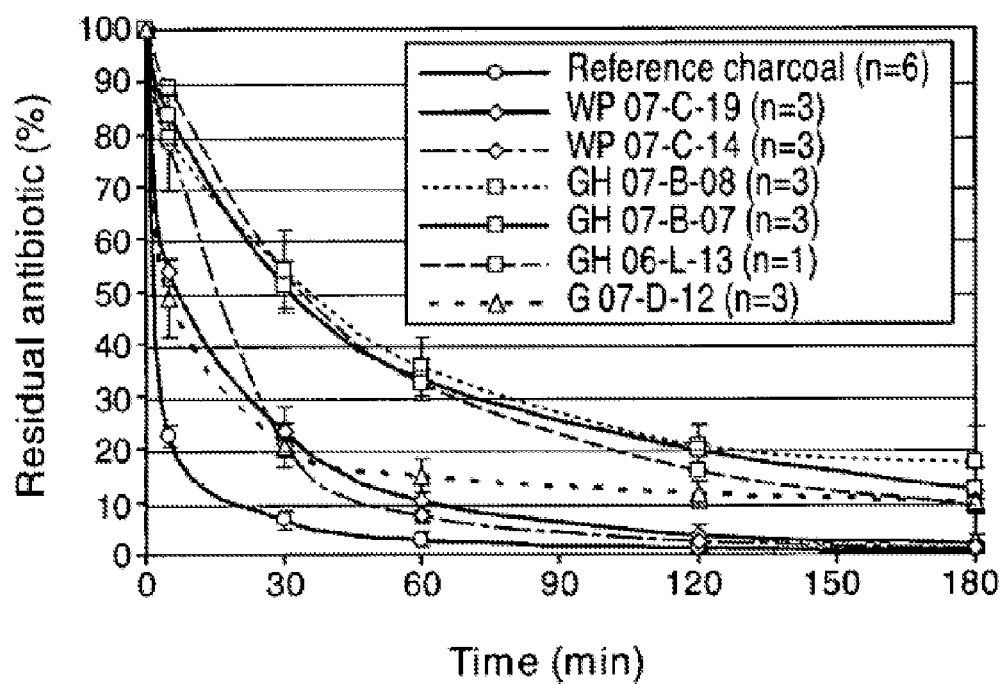
FIG. 5 presents the kinetics of ciprofloxacin removal with a non formulated charcoal taken as reference, and six different formulations of activated charcoal. The initial concentration of ciprofloxacin was 75 µg/ml in 100 ml of simulated colonic medium (pH 7.4). All formulations were added so that the final concentration of activated charcoal was 180 µg/ml. Yellow circles represent 180 µg/ml non formulated charcoal, blue diamonds represent 225 µg/ml WP 07-C-19 pellets, purple diamonds represent 277 µg/ml WP 07-C-14 pellets, red squares represent 212 µg/ml GH 07-B-08 granules, blue squares represent 212 µg/ml GH 07-B-07 granules, green squares represent 212 µg/ml GH 06-L-13 granules and black triangles represent 600 µg/ml G 07-D-12 semi-solid formula, each in 100 ml of SCM, pH 7.4.

The capacity of activated charcoal formulated as described above to adsorb various antibiotics in simulated colonic conditions was studied. FIG. 5 presents, as an example, a comparison of the kinetics of ciprofloxacin adsorption by different activated charcoal formulations and non formulated activated charcoal taken as a reference. The composition of the different tested formulations is described in Table 6. A weight/weight ratio of activated charcoal (excluding additives) to ciprofloxacin of 2.4 was used with both the non formulated charcoal and the six different formulations in order to compare adsorption characteristics. As can be observed in FIG. 5, total removal of ciprofloxacin by unformulated charcoal was achieved after 60 minutes of incubation. The results depicted in FIG. 5 show that pellet formulations WP07-C-14 and WP07-C-19 demonstrated higher adsorption capacity and faster adsorption kinetics than granules (GH 07-B-07, GH 07-B-08, GH 07-L-13) or semi-solid forms (G 07-D-12). The activated charcoal released from the pellets described above retained almost intact adsorption efficiency as compared with unformulated charcoal. TABLE-US-00006 TABLE 6 Reference and composition of different formulations of activated charcoal tested for adsorption of ciprofloxacin in colonic simulated conditions. Dosage form Reference Composition Granules GH 07-B-07 charcoal: 85% L-HPC: 5%, Starch 1500: 10%, Granules GH 06-L-13 charcoal: 85% L-HPC: 5%, Starch 1500: 10%, SDS: 0.2% Granules GH 07-B-08 charcoal: 85% L-HPC: 5%, Starch 1500: 10%, SDS: 0.2% Pellets WP 07-C-14 charcoal: 65% Avicel PH 102: 25%, Kollidon: 5% Kaolin lourd: 5% Pellets WP 07-C-19 charcoal: 80% Avicel PH 102: 15%, Kollidon: 5% Semi-solid G 07-D-12 charcoal: 30% PEG 400: 70%

EXAMPLE 6

Modified (Charcoals or Carbon-Based Adsorbents)

Activated charcoal is obtained by various ways but pharmaceutical grade charcoal is only obtained from vegetal sources. The conditions applied by different manufactured demonstrate that even though the activated charcoal is fulfilling pharmacopoeia specifications, it can demonstrate large variations in adsorption specificity and capacity towards given molecules of interest.

Activated charcoal can be significantly modified to obtain altered specificity and enhanced adsorption capacity by subsequent physical, chemical or combined treatments as described below.

These treatments have the following objectives:

to increase specific surface since adsorption is often a surface phenomenon, to increase mesoporosity of the solid to facilitate the adsorption of molecules whose volume is important as is the case for antibiotics or other molecules such as toxins;

to increase the surface functionality in order to favor the adsorption of molecules of interest, by displacing the adsorption balance via an increase in the adsorption coefficient. Such modifications are a way to increase adsorption specificity.

Physical Treatments

Activated charcoal can undergo subsequent thermal treatments (pyrolysis) at temperatures varying from 600 to 1100° C. with predefined temperature steps and controlled (steady state or flux) atmospheres (nitrogen, argon, helium preferentially).

These treatments significantly increase the specific surface of the activated charcoal leading to an enhancement of its adsorption capacity for molecules of interest.

Chemical Treatments

Preferred treatments are performed at low temperature (lower than 150° C.) and with charcoal under the form of a suspension in a liquid phase. Various controlled chemical treatments can be performed with nitric acid, sulphuric acid, persulphate, permanganate. For all of these oxidants, a broad range of concentrations is considered, with a maximal range from 0.05 M to 14 M, various temperatures, between 25° C. and 105° C., and various durations from 1 min to 120 hours. Hydrogen peroxide can also be used using similar conditions, except that all modifications are carried out at room temperature. For reasons of industrial feasibility, simple treatments such as those described above are preferred. However, treatments with perchloric or orthophosphoric acids as well as washings with hydrofluoric acid (HF) can also be envisaged because some of the target molecules contain fluoride atoms, and such treatments can be a way to significantly increase the interaction specificity with such modified activated charcoal.

Combined Treatments

For such combined treatments, one can consider treatments carried out at extreme temperatures (beyond 150° C., generally beyond 400° C.) and for which the possible modifying chemical agent is in the form of a gas.

Treatments such as the ones used during certain activations of charcoal with oxygen (lower range of temperature to promote modifications instead of combustion), with wet nitrogen (by bubbling in a water tank) and carbon dioxide can be performed. Treatment with carbon monoxide can also be performed but industrial feasibility is limited. Gas flow rate and temperature can have also a significant influence on the characteristics of the modified charcoals obtained, with concomitant increase in specific surface, as well as adsorption capacity and specificity.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. An orally-administrable pharmaceutical composition for site-specific intestinal release of an adsorbent, the composition comprising: a) an adsorbent capable of adsorbing a bacterial or fungal toxin or a pharmaceutically active agent known to cause adverse side effects when they reach the colon, and b) a site-specific delivery system which releases the adsorbent at a desired level of the intestine, wherein the desired level of the intestine is the ileum or the colon, and the composition is substantially devoid of pectin, wherein the adsorbent is selected from the group consisting of activated charcoal, clays, talc, silica, and resins.

2. The pharmaceutical composition of claim 1, wherein the clay is selected from the group consisting of bentonite, kaolin, montmorillonite, attapulgite, halloysite, and laponite or wherein the silica is selected from the group consisting of colloidal silica, mesoporous silica, fumed silica and zeolites.

3. The composition of claim 1, wherein the adsorbent is mixed with one or more pharmaceutically-acceptable carriers selected from the group consisting of starches, lactose, sucrose, glucose, mannitol, silicic acid, carboxymethyl cellulose, alginates, gelatin, polyvinyl pyrrolidone, sucrose, acacia, glycerol, agar-agar, calcium carbonate, starch, cetyl alcohol, glycerol monostearate, non-ionic surfactants, talc, calcium stearate, magnesium stearate, solid polyethylene glycols, sodium lauryl sulfate, coloring agents, and mixtures thereof.

4. The composition of claim 1, wherein the composition is in the form of a molded tablet or pellets prepared by molding a powdered adsorbent moistened with an inert liquid diluent.

5. The composition of claim 1, wherein the composition comprises a coating and/or shell.

6. The composition of claim 5, wherein the coating is a gastro-resistant coating, optionally including a complementary enteric coating designed to provide delayed release of the adsorbent in the ileum or colon the gastrointestinal tract.

7. The composition of claim 6, wherein the coating comprises a film of a polymer which is insoluble in the acid environment of the stomach, and soluble in the neutral environment of the ileum and/or colon.

8. The composition of claim 7, wherein the coating is formed from one or more polymers selected from the group consisting of cellulosic polymers, acrylic acid polymers and copolymers, and other methacrylic resins.

9. The composition of claim 8, wherein the methacrylate resins are those which are commercially available under the tradename Eudragit®.

10. The composition of claim 9, wherein the Eudragit® polymer is selected from the group consisting of Eudragit® L30D-55, Eudragit® L100-55, Eudragit® L-100, Eudragits® NE, RL and RS, and Eudragit FS30D and compatible mixtures thereof.

11. The composition of claim 5, wherein the coating comprises a polymer selected from the group consisting of vinyl polymers and copolymers, azo polymers, chitosan, amylase, guar gum, zein, shellac, and combinations thereof.

12. The composition of claim 1, wherein the adsorbent is activated charcoal formulated by wet granulation with one or more binders selected from the group consisting of sorbitol, starch, cellulose, and cellulose derivatives and compatible mixtures thereof.

13. The composition of claim 1, wherein the composition comprises activated charcoal as the adsorbent and PEG 400 as an excipient.

14. The composition of claim 1, wherein the composition comprises activated charcoal (Norit), Avicel PH102, and polyvinylpyrollidone.

15. The composition of claim 1, wherein the composition comprises activated charcoal, Avicel PH 102, polyvinylpyrollidone, and Kaolin lourd.

16. An orally-administrable pharmaceutical composition for site-specific intestinal release of an adsorbent consisting essentially of:
a) an adsorbent capable of adsorbing a bacterial or fungal toxin or a pharmaceutically active agent known to cause adverse side effects when they reach the colon, and
b) a site-specific delivery system which releases the adsorbent at a desired level of the intestine, wherein the desired level of the intestine is the ileum or the colon, the composition being substantially devoid of pectin,
wherein the adsorbent is selected from the group consisting of activated charcoal, clays, talc, silica, and resins.

17. The composition of claim 16, wherein the adsorbent is mixed with one or more pharmaceutically-acceptable carriers selected from the group consisting of starches, lactose, sucrose, glucose, mannitol, silicic acid, carboxymethyl cellulose, alginates, gelatin, polyvinyl pyrrolidone, sucrose, acacia, glycerol, agar-agar, calcium carbonate, starch, cetyl alcohol, glycerol monostearate, non-ionic surfactants, talc, calcium stearate, magnesium stearate, solid polyethylene glycols, sodium lauryl sulfate, coloring agents, and mixtures thereof.

18. The composition of claim 16, wherein the composition is in the form of a compressed tablet prepared using one or more of a binder, lubricant, inert diluent, preservative, disintegrant, surface-active or dispersing agent.

19. An orally-administrable pharmaceutical composition for site-specific intestinal release of an adsorbent, the composition consisting essentially of:
a) an adsorbent capable of adsorbing a bacterial or fungal toxin or a pharmaceutically active agent known to cause adverse side effects when they reach the colon, b) a site-specific delivery system which releases the adsorbent at a desired level of the intestine, wherein the desired level of the intestine is the ileum, or the colon, the composition being substantially devoid of pectin, and c) a coating and/or shell,
wherein the adsorbent is selected from the group consisting of activated charcoal, clays, talc, silica, and resins.

20. The composition of claim 19, wherein the coating is a gastro-resistant coating, optionally including a complementary enteric coating designed to provide delayed release of the adsorbent in a certain portion of the gastrointestinal tract.

21. The composition of claim 20, wherein the coating comprises a film of a polymer which is insoluble in the acid environment of the stomach, and soluble in the neutral environment of the small intestines and/or colon.

22. The composition of claim 21, wherein the coating is formed from one or more polymers selected from the group consisting of cellulosic polymers, acrylic acid polymers and copolymers, and other methacrylic resins.

23. The composition of claim 22, wherein the methacrylate resins are those which are commercially available under the tradename Eudragit®.

24. The composition of claim 23, wherein the Eudragit® polymer is selected from the group consisting of Eudragit® L30D-55, Eudragit® L100-55, Eudragit® L-100, Eudragits® NE, RL and RS, and Eudragit FS30D and compatible mixtures thereof.

25. The composition of claim 19, wherein the coating comprises a polymer selected from the group consisting of vinyl polymers and copolymers, azo polymers, chitosan, amylase, guar gum, zein, shellac, and combinations thereof.

26. The composition of claim 19, wherein the adsorbent is activated charcoal formulated by wet granulation with one or more binders selected from the group consisting of sorbitol, starch, cellulose, and cellulose derivatives and compatible mixtures thereof.

27. The composition of claim 19, wherein the composition comprises activated charcoal as the adsorbent and PEG 400 as an excipient.

28. The composition of claim 19, wherein the adsorbent consists essentially of a combination of activated charcoal (Norit), Avicel PH102, and polyvinylpyrollidone.

29. The composition of claim 19, wherein the adsorbent consists essentially of a combination of activated charcoal, Avicel PH 102, polyvinylpyrollidone, and Kaolin lourd.

30. A method for treating or preventing adverse effects of a bacterial or fungal toxin on the intestinal flora, comprising administering the pharmaceutical composition of claim 20 to a patient.

31. A method for treating adverse effects of an antibiotic to the intestinal flora, comprising administering a therapeutically effective dosage of an orally-administrable pharmaceutical composition for site-specific intestinal release of an adsorbent, the composition comprising:
   a) an adsorbent capable of adsorbing an antibiotic, and
   b) a site-specific delivery system which releases the adsorbent at a desired level of the intestine, wherein the desired level of the intestine is the ileum or the colon, and the composition is substantially devoid of pectin, wherein the adsorbent is selected from the group consisting of activated charcoal, clays, talc, silica, and resins.

32. The method of claim 31, wherein the activated charcoal has been subjected to one or more physical and/or chemical treatment to modify its properties.

33. The method of claim 31, wherein the clay is selected from the group consisting of bentonite, kaolin, montmorillonite, attapulgite, halloysite, and laponite or wherein the silica is selected from the group consisting of colloidal silica, mesoporous silica, fumed silica and zeolites.

34. The method of claim 31, wherein the composition further comprises a compound that inactivates an antibiotic.

35. The method of claim 34, wherein the compound is an enzyme that inactivates antibiotics.

36. The method of claim 35, wherein the enzyme is a beta-lactamase, an erythromycin esterase or an enzyme that is able to inactivate antibiotics other than beta-lactam antibiotics or erythromycins.

37. The method of claim 31, wherein the composition is administered to a patient, either before, during, or after administration of the antibiotic.

38. The method of claim 31, wherein the composition is in the form of a capsule, a tablet, a pill, a dragee, a powder, a pellet or a granule.

39. The method of claim 31, wherein the adsorbent is mixed with one or more pharmaceutically-acceptable carriers selected from the group consisting of starches, lactose, sucrose, glucose, mannitol, silicic acid, carboxymethyl cellulose, alginates, gelatin, polyvinyl pyrrolidone, sucrose, acacia, glycerol, agar-agar, calcium carbonate, starch, cetyl alcohol, glycerol monostearate, non-ionic surfactants, talc, calcium stearate, magnesium stearate, solid polyethylene glycols, sodium lauryl sulfate, coloring agents, and mixtures thereof.

* * * * *